US00PP08238P

United States Patent [19]

Krug

[11] Patent Number: Plant 8,238

[45] Date of Patent: May 25, 1993

[54] ORANGE TREE NAMED 'SWEET MARTIN'

[76] Inventor: Martin J. Krug, 2069 S. Leonard, Sanger, Calif. 93657

[21] Appl. No.: 756,439

[22] Filed: Sep. 9, 1991

[51] Int. Cl.[5] ..... A01H 5/00

[52] U.S. Cl. ..... Plt./45

[58] Field of Search ..... Plt./45

[56] References Cited

U.S. PATENT DOCUMENTS

| | | | |
|---|---|---|---|
| P.P. 126 | 5/1935 | Robertson | Plt. 45 |
| P.P. 2,818 | 7/1968 | Mabs | Plt. 45 |
| P.P. 2,970 | 6/1970 | Walker et al. | Plt. 45 |

*Primary Examiner*—James R. Feyrer
*Attorney, Agent, or Firm*—Dennis B. Haase

[57] ABSTRACT

A new and distinct variety of navel orange tree, having a maturity period in the early season, as much as two weeks before its parent Washington Navel, at which time both its color and soluble solids/acid ratios is superior to other early varieties, without loss of desirable eating qualities and having large fruit with thick skin, making it more durable, sweet tartness, firm texture and excellent flavor, all of which contributes to its desirablity for eating.

1 Drawing Sheet

BACKGROUND OF THE VARIETY

The present invention relates to a new and distinct variety of navel orange, which I refer to as "Sweet Martin", displaying early maturity, both in color and soluble solids/acid ratios, having a smaller well developed and more deeply imbedded navel opening, making it more cosmetically acceptable, and having the characteristics of maturing in the early season. This variety was developed from a spontaneous sport limb.

ORIGINAL AND ASEXUAL REPRODUCTION OF THE NEW VARIETY

This novel orange was derived from a grove situated in Sanger, Calif., which was planted between 1958 and 1962. As the trees reached maturity and started bearing fruit, a spontaneous sport limb was discovered on which the fruit gained color before the rest of the tree and the rest of the grove. The particular tree in question was planted in 1962 on Trifoliate orange rootstock and budded to an Old Line Washington navel orange cultivar.

This early maturing branch was marked and monitored each year to determine any abnormalities that might otherwise make it distinctive or novel.

During the blossom period to the preharvest fall months, no distinctive differences were noted until color break appeared, usually mid-October. This particular fruit was on schedule with the remainder of the grove, but upon daily inspection, it was noted that in the month of coloring this fruit accelerated and in a period of ten days it had gone from a yellow-green to orange color, while the remainder of the grove was at least two weeks later in coloring. This phenomenon was observed for a sufficient period to prove to be consistent.

In February 1985, three Troyer rootstock seedlings were acquired from McEwan Nursery in the Visalia, Calif. area. These seedlings were one year old and were planted in the subject orange grove.

In April 1985, three buds from the sport branch were removed and inserted into the Troyer seedlings. Two additional Troyer rootstock seedlings were acquired and planted in January 1986 and in April of that year these two seedlings were budded from the sport branch.

These five trees of the new variety have been growing in the orchard and the oldest have produced fruit for the past three season. All five trees are true to the parent bud sport and the fruit colors about two weeks in advance of the remainder of the grove.

On Oct. 25, 1988, fruit was delivered to the Bee Sweet Citrus Packinghouse in Fowler, Calif. for testing. The new early variety tested 10.1 on the soluble solids-/acid ratio, while fruit from the remainder of the grove tested 7.8 soluble solids/acid ratio. Fruit samples were again delivered to Bee Sweet Packing for testing on Oct. 29, 1989. The new early variety tested 10.2 soluble solids/acid ratio, while the remainder of the grove tested 7.9 soluable solids/acid ratio.

A test was conducted by Bee Sweet Citrus on Oct. 27, 1990 with their portable testing unit in the grove. The new variety tested 8.0 soluable solids/acid ratio, while the remainder of the grove tested 7.1 soluable solids/acid ratio.

A second test done in the grove with this new orange on Nov. 5, 1990, produced an 8.8 soluable solids/acid ratio. It should be noted that other early varieties of navel oranges are able to test because the pulp lacks acid, thus lacking the tartness that consumers so desire. This new variety is quite tart, yet sweet, much earlier in the season.

Fruit samples of this new variety were taken to Bee Sweet Citrus Packing where it was "sweat for color" for 72 hours. The fruit was colored to Maerz & Paul, 2d Ed., plate 9, 9-K. Other early navel varieties (Tule Gold) that had been picked on the same date and "sweated" for 96 hours colored Maerz & Paul, 2d Ed., plate 9, 5-L.

The new variety fruit picked on Nov. 17, 1990 was placed in cold storage until Jun. 12, 1991, and was found free of breakdown with no loss of fruit due to bacterial invasion. The pulp remained fresh and sweet, and wide commercial acceptance is anticipated since tests show that the fruit handles and stores well while retaining its distinctively better color.

The new variety is very compatible when budded to Troyer rootstock and produces a uniquely smooth bud union, practically undetectable; after six years no bud union disorders are observed.

One hundred fruit of the new variety and 100 fruit of the remainder of the grove were inspected at random for enlarged or protruding navel ends in November 1990. Seventy two fruit of the new variety had navel openings smaller than ¼ inch where only 48 fruit from the remainder of the grove had this characteristic, making the new variety more cosmetically acceptable and improving the pack out values.

SUMMARY OF THE VARIETY

The instant variety, developed through the above method, was singled out by virtue of its unique and novel characteristics in that it matures, both in color and soluable solids/acid ratios, a minimum of two weeks before the conventional parent Washington navel cultivar without loss of the desirable eating qualities of the parent varieties. An added benefit if that it typically matures and is available prior to Federal Marketing Orders becoming effective. This, in addition to excellent harvesting, handling, packing and cold storage characteristics, make it competitive with parent varieties harvested in mid-December.

Also, when compared with earlier varieties such as Tule Gold and Skaggs Bonanza, it has superior color and eating qualities. Its handling characteristics are, likewise, superior in that it resists splitting during handling and spotting during the sweating operation. This new variety tends to have good acid in the early part of the season.

BRIEF DESCRIPTION OF THE DRAWINGS

The accompanying drawing illustrates typical specimens of the fruit and foliage of my new variety as grown in the San Joaquin Valley of California. Four specimens are shown, one of which is in the side elevation; one from the apex view; one from the distol view illustrating the navel; and a specimen in a section side elevation illustrating the internal texture and color of the flesh.

DETAILED DESCRIPTION

The following is a detailed description of my new variety. Each color reference is with respect to the Maerz and Paul Dictionary of Colors, except in instances where terminology having generally accepted meaning is employed.

Parentage: Old Line Washington Navel and Trifoliate orange rootstock.

Budding: Scions of this plant have shown excellent graft compatibility on Troyer citrage rootstocks to a point that the graft union becomes inconspicuous within a few years. Clones of the tree have been observed to reliably maintain the distinguishing characteristics of the tree through several generations of trees attained by budding.

Locality where grown and observed: Near Sanger, County of Fresno, Calif.

TREE

Size: Normal as compared with other orange cultivars.

Vigor: Vigorous, production. A 30-year old parent tree has a trunk circumference below the bud union of 27½ inches as compared with 11½ inches on the 7-year old new variety and a circumference above the bud union of 13½ inches as compared with 9½ inches on the new variety. Average length of new terminal shoots is 22 inches.

Shape: Bushy with well rounded top — normal with other orange cultivars.

Productivity: Considered good as compared with other navel tree varieties. Unlike Old Line Washington Navels which show strong tendencies to bear heavy and light in alternate years, the new variety appears to have no heavy or light bearing seasons as to the volume or numbers of fruit, but bears consistently.

Regularity of bearing: consistent to other navel varieties.

Trunk: Extremely smooth bud union.

*Diameter in relation to length.*—2⅜ inches (6.03 cm.) diameter; 23 inches (58.42 cm.) in length.

*Surface characteristics.*—Color, plate 23A-1; smooth to slightly abrasive.

*Canopy and height.*—The parent tree has a canopy diameter of 9 feet 10 inches with a height of 11 feet 4 inches as compared to the new variety, having an average canopy diameter of 4 feet 2 inches and a height of 7 feet 2 inches.

Branches:

*Size.*—Average when compared with the parent tree.

*Surface character.*—Surface texture of branches is identical to that of the trunk. There is an absence of thorns, which is a significant difference from the parent tree and Old Line Washington Navel variety.

*Color.*—Plate 23A-1.

*Lenticels.*—Irregular patterns. Number: 600 to 800 observed on immature branches. Size: Globose in shape; 0.0156 inches (0.39 mm) in diameter.

*Thinning requirements.*—The new variety has a definite tendency to produce a vertical structure as opposed to a bush type canopy in the parent, thus allowing for less pruning and shaping of the tree in its early years to remove the skirts from the ground. Only after the fifth or sixth year does the new variety take up a bushy appearance and an increase in diameter of the canopy. Early season aborted fruit is less than the parent, partially because of few flowers and the tendency for flowers to appear on new terminals where the leaves outnumber the flowers.

Leaves:

*Size.*—Average.

*Length.*—3½ to 5 inches (8.89 cm. to 12.7 cm.).

*Width.*—2 to 2⅜ inches (5.08 cm. to 6.2 cm.).

*Shape.*—Elliptic to oblong, ovate.

*Venation.*—Midrib to margin.

*Color.*—New Flush Growth: Upward disposed surface, Plate 22 7-L; downward disposed surface, plate 18 9-J.

*Older mature.*—Upward disposed surface, Plate 23 10-J; downward disposed surface, Plate 21 7-L.

*Marginal form.*—Smooth to slightly serrated.

*Glandular characteristics.*—Globose stomata, irregular spacing.

*Petiole.*—Shape: Winged. Length: ⅝ to ⅞ inches (1.59 cm. to 2.22 cm.). Thickness: 5/16 to 7/16 inches (0.8 cm. to 1.11 cm.).

*Stem glands.*—Number: 600 to 800 per square inch. Arrangement: Irregular. Size: 0.0156 inches (0.39 mm.). Type (Globose and Reniform): Globose. Color: Plate 21, J-7.

*Stipules.*—Normal with other navel cultivars.

Flower buds:

*Size.*—5/32 to ¼ inches in diameter, may be elongated to 7/16 inches in length.

*Shape.*—Globose to slightly elongated.

*Surface.*—Smooth.

*Other distinguishing characteristics.*—Color.—Plate 9A-1.

Flowers:

*Date of bloom.*—Variable. From first to third week in April.

*Size.*—Variable. Between $\frac{5}{8}$ and $\frac{7}{8}$ inches in length.

*Color.*—Petal, Plate 9A-1; Septal, Plate 9K-1; Floral Disc, Plate 10F-1; Stamen, Plate 19A-1.

*Anthers.*—Plate 18K-1.

*Other distinguishing characteristics.*—Old Line Washington Navels have a tendency to bloom heavy (pop corn bloom) and light in alternating seasons. The new variety has a more consistent all over flower set with less clustering of flowers and more flowering on the interior of the trees.

Fruit:

*Maturity.*—Early, mid to late October.

*Size.*—Uniformity: Globose to depressed globose. Fruit of the new variety is larger than the parent, exhibiting better than average uniformity at harvesting as to color, size, shape and ripeness. Diameter: $2\frac{3}{8}$ to 3 inches.

*Form.*—Uniformity: Average. Symmetrical: Average Ventral surface: Rounded, but occasionally slightly flat. Stem Cavity: Rounded, 7/32 inches diameter, 1/16 inch deep. Base: Rounded to slightly flat at navel opening. Apex: Slightly rounded. Navel ends: Navel ends are small, with approximately 72% being less than one-quarter inch, well developed and more deeply embedded than the parent, being flat with the surface of the peel. When exposed, the navel ends are flower shaped and very uniform. Stem: Length: Average — $\frac{1}{2}$ inch. Caliper: $\frac{1}{8}$ inch diameter.

*Skin.*—Thickness: Average — 7/32 to 9/32 inches. Texture: Smooth to slightly dimpled, glabrous, almost waxy in appearance. Tendency to crack: Average Color: Plate 10, G-9. Pubesence: None. Oil glands: Oil glands number 55–80 cm. sq., consistent in size and randomly spaced (not uniform as appearing in rows), mature fruit having a color of Plate 12-J7 and Plate 19-G5 on immature fruit.

*Flesh.*—Color: Plate 10, L-7. Seeds: Seeds have been observed in a sparse and random distribution; considered to be seedless, as is the Old Line Washington Navel. Juice: Average. Segments: Number range 10–12, average 11 as compared with the parent variety having an average of 9 to 10.

Segments are more easily separated than on the parent tree. Flavor: Mild, sweet and slightly tart. Texture: Firm, segmented and easily separated. Fibers: None. Ripening: Even.

On tree storage: Good to excellent characteristics into early May of the following season with no tendency to regreen and the peel maintaining a youthful appearance.

Use: Principally fresh eating orange.

Keeping quality: Excellent.

Shipping quality: Excellent.

Resistance to disease: Similar to other varieties of navel oranges.

Although this novel variety of orange tree possesses the described characteristics as a result of the growing conditions in Fresno County, Calif., in the central portion of the San Joaquin Valley, it is to be understood that variations of the usual magnitude in characteristics incident to growing conditions, fertilization, pruning and pest control are to be expected.

Having thus described and illustrated my new variety of orange tree, what is claimed as new and desired to be secured by Letters Patent is:

1. A new and distinct variety of navel orange tree, as described and illustrated, having no thorns, having a maturity period in the early season, both in color and soluable solids/acid ratios, and without loss of desirable eating qualities and having superior color, and having large fruit with thick skin, small, embedded navel ends, ease of segment separation, sweet tartness, firm texture and excellent flavor.

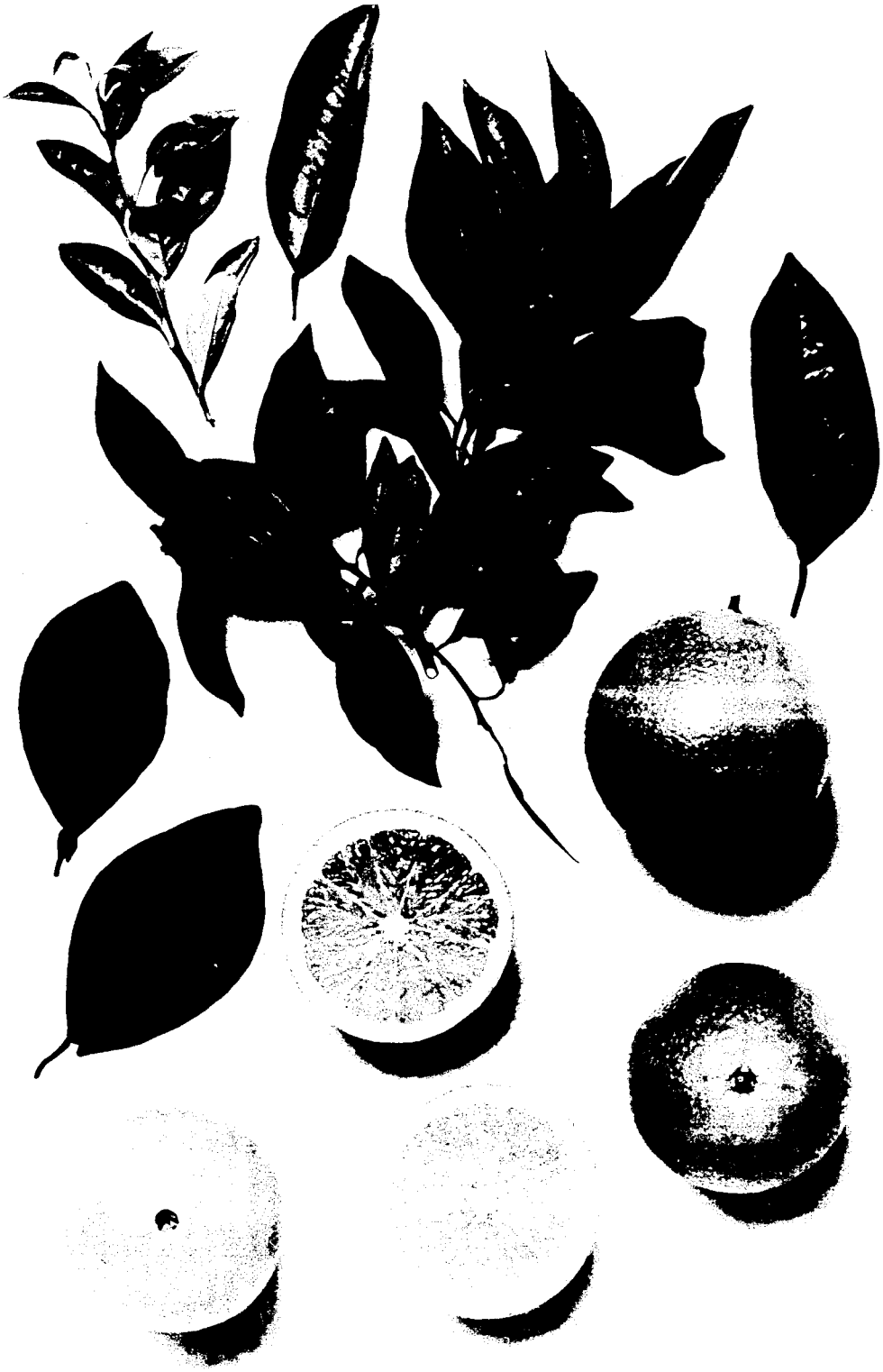

* * * * *